(12) United States Patent
Bou et al.

(10) Patent No.: US 8,114,449 B2
(45) Date of Patent: Feb. 14, 2012

(54) ALCOHOL-TOLERANT MALOLACTIC STRAINS FOR THE MATURATION OF WINES WITH AVERAGE OR HIGH PH

(75) Inventors: Magali Bou, Seysses (FR); Sibylle Krieger, Stuttgart (DE)

(73) Assignee: Danstar Ferment AG, Zug (CH)

( * ) Notice: Subject to any disclaimer, the term of this patent is extended or adjusted under 35 U.S.C. 154(b) by 172 days.

(21) Appl. No.: 12/604,436

(22) Filed: Oct. 23, 2009

(65) Prior Publication Data

US 2010/0040730 A1 Feb. 18, 2010

Related U.S. Application Data

(62) Division of application No. 10/560,086, filed as application No. PCT/FR2004/001421 on Jun. 9, 2004, now Pat. No. 7,625,745.

(30) Foreign Application Priority Data

Jun. 12, 2003 (FR) .................................. 03 07046

(51) Int. Cl.
| | | |
|---|---|---|
| C12C 11/00 | (2006.01) | |
| C12C 3/08 | (2006.01) | |
| C12C 7/00 | (2006.01) | |
| C12G 1/00 | (2006.01) | |
| A61K 35/74 | (2006.01) | |
| C12N 1/20 | (2006.01) | |

(52) U.S. Cl. ................. 426/11; 426/12; 426/13; 426/14; 426/15; 426/52; 426/61; 435/252.9; 424/93.45

(58) Field of Classification Search .................... 426/11, 426/12, 13, 14, 15, 52, 61; 424/93.45; 435/252.9
See application file for complete search history.

(56) References Cited

U.S. PATENT DOCUMENTS

| 4,666,849 A | 5/1987 | Daeschel et al. |
| 5,077,060 A | 12/1991 | Prahl |
| 5,607,854 A | 3/1997 | Prahl et al. |
| 6,284,518 B1 | 9/2001 | Henick-Kling et al. |
| 7,112,346 B2 | 9/2006 | Prahl et al. |

OTHER PUBLICATIONS

Carbo R et al. "Aislamiento y Selection de Bacterias Lacticas en Vino Isolation and Selection of Lactic Acid Bacteria in Wine Isolamento E Selezione Di Batteri Lattici Nel Vino" Rivista di Viticoltura di Enologia, Scarpis, Treviso., IT vol. 48, No. 4, 1995, pp. 29-38, XP009021609 ISSN: 0370-7865 p. 31-p. 37.

Carrie C et al.: "Comparison of Commercial Preperations of Lactic Acid Bacteria for Direct Inoculation, for Control of Malolactic Fermentation of Merlot Wines Comparison de Preperations Commerciales de Bacteries Lactiques a Ensemencement Direct, en Vue de Gerer la Fermentation Malolactique du Merlot" Revue Des Oenologues et Des Techniques Vitivinicoles et Oenologiques, Union Nationale Des Oenologues Fracnce Bourgogne, 2002.

Pilone G J: "A New Zealand Experience in Direct-Vat Inoculation for Malolactic Fermentation" Australian and New Zealand Wine Industry Journal, Australian Industrial Publishers. Adelaide, AU vol. 10, No. 2, May 1995, pp. 169-173, XP009023865 ISSN: 0819-2421 the whole document.

Liu S-Q et al: "Growth and Metabolism of Selected Lactic Acid Bacteria in Synthetic Wine" American Journal of Enology and Viticulture, XX, XX, vol. 46, No. 2, 1995, pp. 166-174, XP009021611 ISSN: 0002-9254 the whole document.

Joyeux A et al: "Comparaison de Diverses Preparations Industrielles de Bacteries Lactiques Reactivees Pour Stimuler la Fermentation Malolactique Comparison of Various Reactivated Industrial Preparations of Lactic Acid Bacteria for Stimulation of Malolactic Fermentation" Connaissance de la Vigne et du Vin, Vigne et Vin Publications Internationales, Bordeaux, FR, vol. 19, No. 3, 1985, pp. 149-159, XP00902986 ISSN: 0010-597X p. 151, p. 153-p. 157.

Fuster A et al: "Improvement of the quality and typicalness of wines with the aid of new biological techniques" Revue Francaise D'Oenologie, Lallemand SA, 130 Route D'Espagne, BP 1021, 31023 Toulouse, France, 2002, pp. 28-31, XP009027063 the whole document.

Edwards C G et al: "Occurrence and Characterization of Lactic Acid Bacteria From Washinton State Wines: Pediococcus SPP" American Journal of Enology and Viticulture, XX, XX, vol. 43, No. 3, 1992, pp. 233-238, XP009021610 ISSN: 0002-9254 the whole document.

Liu S Q: "Malolactic fermantation in wine—beyond deacidification" Journal of Applied Microbiology 92 (4) 589-601, New Zealand Diary Res. Inst., Palmerston North, New Zealand. E-Mail Shao.Lui(a) NZDRI.ORG.NZ, 2001, XP002272274 the whole document.

*Primary Examiner* — Herbert J Lilling

(74) *Attorney, Agent, or Firm* — Young & Thompson

(57) ABSTRACT

Lactic bacterial strains of the genera *Lactobacillus* and *Pediococcus* which are capable of initiating and carrying out a complete malolactic fermentation on direct introduction, in the dried, frozen or lyophilised state, without a previous acclimatization step, at a concentration of between $10^6$ and $5 \times 10^7$ UFC/ml, into a wine with an alcohol content of 10% or more and an average or high pH level. The resistance to alcohol is apparent with an excellent survival rate on inoculation and a rapid start to the fermentation activity such that the strain i) converts at least 5%, preferably at least 10%, of the malic acid into lactic acid in 5 days after inoculation of the wine and ii) converts at least 10%, preferably at least 25%, of the malic acid into lactic acid within 10 days of the inoculation of the wine.

7 Claims, 3 Drawing Sheets

ALCOHOL-TOLERANT MALOLACTIC STRAINS FOR THE MATURATION OF WINES WITH AVERAGE OR HIGH PH

CROSS REFERENCE TO RELATED APPLICATIONS

This application is a division of application Ser. No. 10/560,086 filed on Dec. 9, 2005; which is the 35 U.S.C. 371 national stage of International application PCT/FR2004/001421 filed on Jun. 9, 2004; which claimed priority to French application 03/07046 filed Jun. 12, 2003. The entire contents of each of the above-identified applications are hereby incorporated by reference.

The present invention relates to a method of controlling malolactic fermentation in wines by direct inoculation with selected lactic bacterial strains.

It relates to selected alcohol-resistant lactic bacterial strains, capable of initiating and achieving a complete malolactic fermentation (MLF) when they are introduced, without a prior acclimatisation step, into a wine with average to high pH. This resistance to alcohol is used to advantage in a method of supervising the MLF in a wine with average to high pH, and this is also the subject-matter of the present invention.

Malolactic fermentation (MLF) is the decarboxylation of the malic acid into lactic acid, resulting from the metabolic activity of certain lactic bacteria. Originating from the surface of the grape seeds, the vine leaves, the soil and the winemaking equipment, numerous lactic bacteria are naturally present at all of the stages of the winemaking method and the storing of the wine. However, only a few groups of lactic bacteria are capable of multiplying in the grape juice and above all in the wine, by reason of the conditions of limiting growths. They belong to 4 genuses: *Oenococcus*, *Leuconostoc*, *Lactobacillus* and *Pediococcus*. Three species of *Pediococcus* and seven species of *Lactobacillus* are commonly encountered in wine (Kunkee, 1967, Adv. Appl. Microbiol., vol. 9, pp. 235-279), while *Leuconostoc* and *Oenococcus* are each represented there by a single species (*Leuconostoc mesenteroides* and *Oenococcus oeni*, respectively).

The reduction in the acidity and the modification of the aromas of the wine which arise from the MLF are considered as beneficial to the quality of the wine. This secondary fermentation contributes in addition to the biological stabilisation of the wine. Its successful achievement is therefore of great importance for obtaining wines of quality, and this has led the producers to research means for controlling its initiation and its development.

In traditional winemaking, the MLF is produced by means of the spontaneous growth of an indigenous flora of lactic bacteria. The process of MLF begins of its own accord, when the malolactic flora is sufficiently developed, that is to say in a random manner between the end of alcoholic fermentation and several weeks, even several months, after the alcoholic fermentation. When the malolactic bacteria reach a concentration of about $10^6$ UFC/ml in the medium, they enter an active metabolic phase and start the fermentation of the malic acid. In these conditions, *Oenococcus oeni* is the species most frequently responsible for the MLF. In fact, if at the start of alcoholic fermentation a predominance of the homofermentary *Lactobacillus plantarum* and *Lactobacillus casei* species is observed, these disappear when the alcohol content increases. After alcoholic fermentation, it is the species *Pediococcus* and *Oenococcus*, depending on the pH, which predominate and finally reach the critical concentration to start the MLF.

Several methods, intended to control the start and the development of the MLF better, have been proposed, based principally on the induction of the MLF by inoculation of the musts or the wines with selected lactic bacterial strains. In general, strains of *Oenococcus oeni* are used, this species being known to be best suited to MLF.

A first method consists of inducing the MLF by means of a non-proliferating biomass of *Oenococcus oeni*. Because the bacteria act in this case like an enzymatic preparation, the complete degradation of the malic acid is only obtained with a massive inoculation, namely at least $10^8$ UFC/ml, and this represents much too high a cost to find any real practical application.

A second method consists of introducing preparations of *Oenococcus oeni* into the winemaking vat before the start of the alcoholic fermentation, when no alcohol has yet been produced and when the must is rich in nutrients. This method has the advantage that the preparations can be added directly to the must in the freeze-dried or frozen state, so that they are not subjected to alcoholic stress which would be seriously prejudicial to them. But the results are not satisfactory, more especially because of the competition between lactic yeasts and bacteria: one of the two populations multiplies more rapidly and can supplant the other, more especially under the influence of the pH of the medium. In addition, since *Oenococcus oeni* is heterofermentary, it can use the sugar as a substrate to produce acetic acid. Because of this, the risk of seeing a production of volatile acidity by the lactic bacteria is strongly dissuasive for the wine growers (Ribereau-Gayon et al., 1975, Sciences et techniques du vin, Volume III, Dunod, Paris).

Faced with this problem, homofermentary strains of *Lactobacillus plantarum* were resorted to, so that there is no production of acetic acid from the sugars present in the must or in the fruit juice, and therefore no increase in the volatile acidity of the wine (patent application EP 0 398 957). The selected strains are introduced into the must or the fruit juice, before or in the first moments of the AF. However, since these malolactic bacteria are incapable of surviving in a fermented wine, the degradation of the malic acid slows down and stops when the alcohol level reaches 5%. Finally, the malic acid is not totally degraded, and the wine obtained is not bacteriologically stable.

Another solution to avoid the production of volatile acidity from the sugars may consist of sowing the wine only after the alcoholic fermentation, when the sugar level is minimal. The preparations of lactic bacteria inoculated into the winemaking vats must in this case be capable of surviving despite the stress due to an already high degree of alcohol in the medium, the lactic bacteria being all the more sensitive to the stress in that they are introduced into the medium in the freeze-dried or frozen state.

Preparations of *Oenococcus oeni* have been commercially available for several years for sowing wine after alcoholic fermentation. A pre-culture in a wine-enriched medium is recommended, to avoid the important drop in the cellular population during the inoculation into the alcoholised medium. For example, an incubation at 25° C. during 1 to 6 days permits the survival of the bacteria to be improved by placing them in a suitable physiological state. This "reactivation", also called "acclimatisation", must permit the resistance mechanisms of the cells subject to an increased alcohol content to be induced, thereby rendering possible an increase in the bacterial population and a resumption of the metabolic activity (Lafon-Fourcade et al., 1993, Conn. Vigne Vin, Vol. 17, pp. 55-71). This method, although efficient, needs time and effort, and requires some microbiological knowledge.

The time of pre-culture and the moment of introduction must be precisely observed if there is not to be a significant loss of viability, and this represents a serious constraint during the harvesting period.

More recently, another path has been explored, to provide preparations of lactic bacteria which respond to the double requirement of being able to be inoculated into a wine in the freeze-dried or frozen form, without loss of viability despite the alcoholic degree, and this permits in particular the MLF to be achieved in shorter periods of time without increasing the biomass produced. The patent EP 635 050 describes a method of inducing the malolactic fermentation by inoculation of a wine with a freeze-dried culture of alcohol-resistant lactic bacteria belonging to the genus Oenococcus oeni, without a prior acclimatisation stage. The selected strains of Oenococcus oeni have a high survival rate which renders possible the start-up of the MLF even at low production concentrations ($1.10^6$ to $5.10^7$ CFU/ml) and in the presence of alcohol at levels of between 10.5% and 13%. In the defined conditions, and for a pH of between 3.2 and 3.6, the cells rapidly enter into the active phase of malolactic fermentation.

Although these freeze-dried preparations of Oenococcus oeni for direct sowing have proved their usefulness in diverse types of wines, there are numerous cases in which their use is not satisfactory. In fact, the pH of the wine is an essential factor which is involved in the selection of the species which will carry out the MLF.

However, a large proportion of the red wines currently produced come from warm regions (such as, for example, southern Europe). These wines have quite a high pH, that is to say in the order of 3.5 or higher than that value, and this encourages the bacterial growth and primarily the development of the indigenous malolactic or other bacteria. These bacteria, which are poorly resistant to pHs lower than 3.5, are then favoured to the detriment of Oe. oeni.

This leads to two types of problems. On the one hand, although the MLF starters based on Oe. oeni, which are inoculated into the vats after the alcoholic fermentation, are resistant to alcohol, their rehydration and their acclimatisation require a certain time before any fermentation activity is recommenced. However, since the indigenous microflora encourages high pHs, undesirable species may develop more rapidly and supplant Oe. oeni. The inoculated bacterial population regresses to below the critical mass of $10^6$ UFC/ml, or even never reaches it. The degradation of the malic acid cannot be completely achieved or cannot even be initiated at all.

On the other hand, at pHs encouraging bacterial growth, the spontaneous start-up of the MLF by one or more indigenous malolactic strains frequently occurs, even before the alcoholic fermentation is complete, and at a stage in the process where the sugars are still present in a notable quantity, militating against the introduction of heterofermentary lactic bacteria into the medium.

In the two cases, the control of the MLF is simply not possible, since the risk is great that it will be carried out by non-specific bacteria, the characteristics of which are not known. The dominant indigenous species may in particular consume several substrates and produce toxic compounds, or lead to unpleasant organoleptic modifications and other negative effects on the wine.

By way of example, certain strains of Lactobacillus brevis can be mentioned which are capable of metabolising the tartaric acid (colour-changing disease), and this reduces the total acidity and increases the volatile acidity. Certain strains of Lactobacillus brevis and Lactobacillus buchneri are capable of degrading the glycerol, the metabolites produced then playing the role of precursor of the acrolein, which reacts with the tannins of the wines and gives a bitter taste. Numerous malolactic strains, of Pediococcus but also of Lactobacillus brevis and certain strains of Oenococcus oeni, may decarboxylate the aminated acids into biogenic amines, such as histidine into histamine, which may be at the origin of severe allergic reactions in sensitive people. Leuconostoc mesenteroides, Lactobacillus brevis and other species, more especially Pediococci, are responsible for ropy wines, a disease of wines caused by the production of exocellular polysaccharides which increase the viscosity of the wine.

The presence of such lactic bacteria within an indigenous microflora is a widespread phenomenon. The complexity of this microflora reinforces the risks that at least one undesirable strain is present in the must, and the mean or high pH values give it the opportunity to develop rapidly therein. All of these metabolic reactions participate, in one way or another, in the alteration in the quality of the wine, and are responsible for serious economic losses.

The producers, who have quantitative aims, but also qualitative aims in relation to the products in order to respond to the expectation in the market place, must be able to control as much as possible the winemaking method, whatever the pH of the wine, and limit the risks of undesired evolution throughout the process. They wish to have starters for the MLF available which are suitable for modern conditions of production and the exigencies of consumers and which best guarantee them against these risks.

The object of the present invention is to respond to this need. In an unexpected manner, the solution resides in the selection of alcohol-resistant lactic bacterial strains belonging to the species Lactobacillus and Pediococcus. They are capable of initiating and of achieving a complete MLF when they are introduced without a prior acclimatisation stage into a wine with average to high pH. This resistance to alcohol, hitherto unknown with the lactic bacteria of these species, reveals itself, on the one hand, by an excellent survival rate at the time of inoculation and, on the other hand, by a rapid start-up of the fermentation activity.

These strains, apart from the fact that they are tolerant to alcohol, have a homofermentary metabolism, permitting them to be inoculated into the wine before the end of the alcoholic fermentation, without producing volatile acidity.

Figure 1:
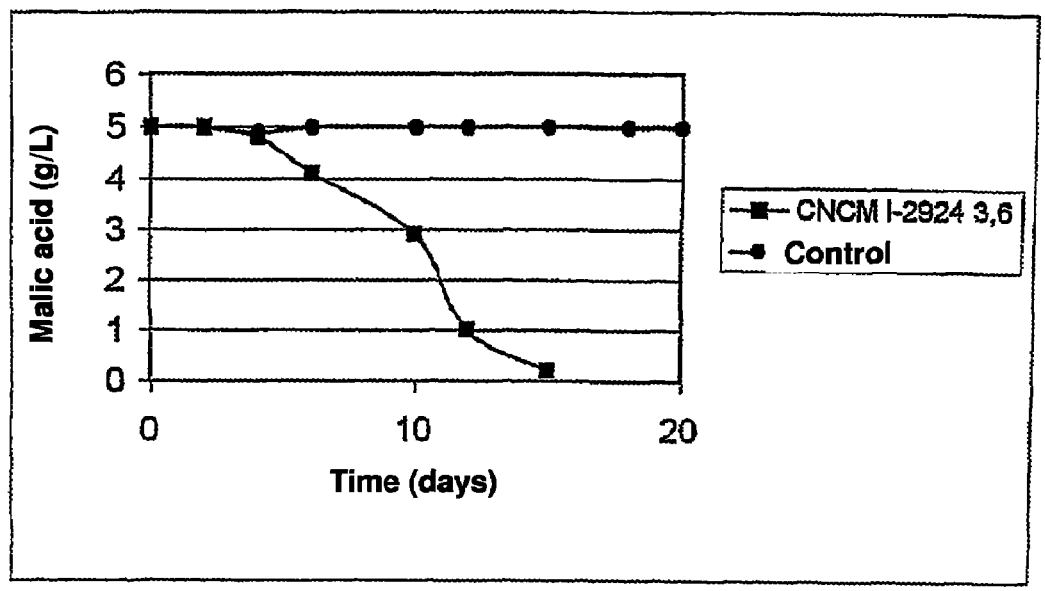
FIG. 1 shows the kinetics of degradation of the malic acid in the test wine at pH=3.6, after inoculation of a freeze-dried preparation of L. plantarum CNCM I-2924.

The combined characteristics of a resistance to alcohol and a rapid growth at average or high pH confer, on the strains according to the invention, the essential advantage of developing more rapidly than the indigenous flora, even at pHs which encourage the growth of the latter. The particularly advantageous result of this is that the indigenous species cannot develop, and are thus prevented from producing undesirable compounds. Sowing in the course of alcoholic fermentation is possible without harming the quality of the wine, and this offers an additional guarantee that the MLF is achieved under the permanent control of the winemaker.

This result is all the more surprising in that the selected strains which meet the exigencies described above belong to the species *Lactobacillus* and *Pediococcus*. These lactic bacteria have until now been excluded from use in an alcoholic medium, in particular because they are rarely present in the alcoholised fermentation media and even less so in the wines. The rare attempts to overcome this a priori have led to disappointing results.

For example, it has been seen above that sowing with preparations of *Lactobacillus plantarum* before alcoholic fermentation did not permit complete MLF because of the loss of activity when the alcohol degree reaches 5%. More recently, this state of affairs was confirmed by the work carried out at the University of Rioja in Spain (Tenorio et al., 2002, XIII Congreso de Microbiologia de los Alimentos, University of Rioja). Two strains of each of the species *Oenococcus oeni* and *Lactobacillus plantarum*, selected from among the indigenous flora, were inoculated at $5.10^6$ UFC/ml into a wine from the Rioja region (southern Spain) after alcoholic fermentation. The strains *Oe. oeni* prevailed in the medium and permitted a good development of the MLF, whilst the strains *L. plantarum* regressed as far as no longer being detectable at the end of the MLF. These results show, once more, that when *Lactobacillus* is introduced into an alcoholised medium, it deteriorates and is not capable of fermenting the malic acid into lactic acid.

Moreover, it is well-known that lactic bacteria have a greatly reduced resistance to stress after drying, freeze-drying or freezing. When they are subjected to unfavourable conditions, such as a high alcoholic degree, their rate of survival decreases drastically, and their fermentation activity can only start after a greater or shorter period of adaptation to the medium. To initiate the MLF, it must in addition reach a concentration in the order of $10^6$ UFC/ml, and this will often necessitate a phase of cellular multiplication which permits the population to be re-formed.

The present invention also provides a response to this problem by means of new selected malolactic bacterial strains belonging to the genuses *Lactobacillus* and *Pediococcus*, these genuses being capable of initiating and achieving the MLF when they are introduced directly in the dried, freeze-dried or frozen state into a wine with average or high pH.

A method of inducing the MLF by direct inoculation of these alcohol-resistant malolactic bacteria is also an object of the present invention.

A fermentation medium, such as a must based on grape juice or other fruit juice, in which the alcohol quantity produced by alcoholic fermentation is at least 5% by volume, will be called "the wine". This wine may have reached its maximum alcoholic degree if the alcoholic fermentation is ended. The alcohol contents are expressed by the volume of alcohol in relation to the total volume.

A wine in which the MLF has completely developed, that is to say in which the malic acid content is less than 0.2 g/l, will be called "the mature wine" or "the wine at maturity". This mature wine is microbiologically stable, unlike immature wine.

For a wine, an average pH will be in the order of 3.5 to 3.6, and a high pH will be able to vary from about 3.6 up to the maximum pHs encountered in wines, namely about 4.0, or even more.

By "direct inoculation" is meant the introduction into the fermentation medium of selected lactic bacteria, without a prior stage of acclimatisation or adaptation to the medium, at an economically acceptable concentration, that is to say of between $10^6$ and $5.10^7$ UFC/ml of medium. A simple rehydration of 20 minutes in water at 22° C. can be effected.

The advantageous properties of the selected strains according to the invention are revealed by their capability of entering into an active fermentation phase practically without latency time, in order to initiate the MLF within a short period of time, despite the unfavourable conditions of the medium.

In practice, this translates by the fact that, from the first days after bacterial inoculation, large fractions of the malic acid present in the medium are transformed into lactic acid. Once the MLF process is initiated, the inoculated bacteria retain their predominant position in the medium and ensure the good development of the MLF until the substrate is exhausted, while guaranteeing that the mature wine finally produced will be exempt from undesirable compounds.

It is important to note that the strains according to the invention are resistant to alcohol even in conditions which habitually induce great stress and lead to cellular deterioration, in particular during inoculation in the dried, freeze-dried or frozen form without a prior acclimatisation stage.

Thus, a selected lactic bacterial strain according to the invention, belonging to the genus *Lactobacillus* or *Pediococcus*, has the capability of effecting the conversion of malic acid into lactic acid so that, when it is introduced at a concentration of between $10^6$ and $5.10^7$ UFC/ml, directly in the dried, freeze-dried or frozen state, into a wine which has an alcohol degree of 10% or more and a pH greater than or equal to 3.5, i) it converts at least 5%, and preferably at least 10%, of the malic acid into lactic acid in 5 days after inoculation of said wine, and ii) it converts at least 10%, and preferably at least 25%, of the malic acid into lactic acid in 10 days after inoculation of said wine.

In a particularly advantageous manner, a lactic bacterial strain according to the invention has a fermentation activity such that, when it is introduced at a concentration of between $10^6$ and $5.10^7$ UFC/ml, directly in the dried, freeze-dried or frozen state, into a wine which has an alcohol degree of 10% or more and a pH greater than or equal to 3.6, iii) it converts at least 10%, and preferably at least 15%, of the malic acid into lactic acid in 5 days after inoculation of said wine, and iv) it converts at least 25%, and preferably at least 40%, of the malic acid into lactic acid in 10 days after inoculation of said wine.

These strains are therefore particularly viable as starters for the MFL in wines with average or high pH, in the course of or at the end of alcoholic fermentation. This said, their use is entirely possible in usual conditions of pH and alcoholic concentration, their capability of achieving the MLF then corresponding to the performances commonly obtained with other starters for the MLF.

As explained previously, in order to ensure that indigenous bacteria do not develop, it can be viable to inoculate the fermentation medium before the end of the alcoholic fermentation, without risking the production of volatile acidity from the sugar still present in the medium. According to an advantageous characteristic of the present invention, the selected lactic bacterial strains are homofermentary.

In addition, it is interesting that the selected strains are not capable of producing toxic compounds or causing unpleasant organoleptic modifications and other negative effects on the wine. That is why the invention also relates to selected lactic bacterial strains which do not produce biogenic amines from the aminated precursors present in the wine, and do not degrade the glycerol or the tartaric acid. Preferably, the strains according to the invention have all of these properties.

According to one advantageous embodiment, the present invention relates to a lactic bacterial strain which possesses all of the previously defined characteristics and has the capability, when it is introduced directly at a concentration of $2.10^6$ UFC/ml into a wine at a temperature greater than or equal to 18° C., having an $SO_2$ content of between 0 and 15 mg/l, an alcohol content greater than or equal to 10% and a pH of 3.7 or more,
   i) of converting 15% of the malic acid into lactic acid in 5 days after inoculation of said wine, and
   ii) of converting 40% of the malic acid into lactic acid in 10 days after inoculation of said wine.

In a particularly advantageous manner, said lactic bacterial strain has all of the previously defined characteristics and has the capability, when it is introduced directly at a concentration of $2.10^6$ UFC/ml into a wine at a temperature greater than or equal to 18° C., having an $SO_2$ content of between 0 and 15 mg/l, an alcohol content greater than or equal to 10% and a pH of 3.7 or more,
   i) of converting 50% of the malic acid into lactic acid in 5 days after inoculation of said wine, and
   ii) of converting 80% of the malic acid into lactic acid in 10 days after inoculation of said wine.

The strains possess the above characteristics when they are introduced into a wine having an alcohol content of 10%, or even 12% and even 13%. Of course, these strains have identical or better characteristics when they are introduced at an earlier stage into the wine, for example when the alcohol content is still only 5%.

As indicated previously, the selected malolactic bacteria belong, in an unexpected manner, to the genuses *Lactobacillus* or *Pediococcus*, until then considered as incapable of developing in an alcoholised medium. In particular, they are selected from the group formed from *Lactobacillus plantarum, Lactobacillus casei, Lactobacillus delbrückii, Pediococcus acidilactici, Pediococcus damnceus, Pediococcus pentosaceus, Pediococcus parvulus, Pediococcus cerevisiae*.

In particular, the following homofermentary malolactic strains are claimed: *Lactobacillus plantarum* DSM-9916, *Lactobacillus plantarum* CNCM I-2924, Pediococcus acidilactici CNCM MA 18/5M, filed in a culture collection of micro-organisms according to the provisions of the Treaty of Budapest, Rule 6.1.

A preparation of lactic bacteria intended to be used as a starter for the MLF, that is to say for sowing a wine with a view to inducing MLF, may comprise one or more malolactic bacterial strains such as previously defined, and possibly other ingredients known to the person skilled in the art. Such preparations may be in the liquid, dried, freeze-dried or frozen state.

The alcohol-resistant malolactic bacteria described above, or a preparation thereof, are intended to be used for the controlled achievement of the MLF in wines with average or high pH, more especially in a method which is the subject-matter of the present invention.

This method of converting malic acid into lactic acid in a wine which has a pH greater than or equal to 3.5 consists of introducing a preparation comprising at least one lactic bacterial strain such as previously described, directly in the dried, freeze-dried or frozen state, into said wine, at a concentration of between $10^6$ and $5.10^7$ UFC/ml, at a temperature greater than or equal to 18° C., when the alcohol degree has reached at least 10%, and of maintaining the wine in conditions which permit the development of the MLF, to obtain a mature wine, the malic acid content of which is lower than 0.2 g/l.

The method may advantageously be applied to any wine, the pH of which is greater than or equal to 3.5, without upper limit. It is used in a particularly advantageous manner for wines with a pH of 3.6 and more, for which wines the risk of developing undesirable bacteria with a rapid growth is particularly high.

If the winemaker so wishes, and in order to avoid the MLF being started by uncontrolled indigenous bacteria, a preparation of lactic bacteria according to the invention may be introduced into the wine in the course of fermentation, for example when the alcohol degree has reached 5% or more, that is to said when the quantity of sugar present in the wine is still considerable. In this case, the lactic bacteria involved in the sowing preparation are all homofermentary, so as to eliminate the risk of producing volatile acidity.

In addition, the method of converting malic acid into lactic acid, the object of the present invention, is effected preferably by means of a preparation of lactic bacteria which possesses one or more of the following characteristics (the ideal being that they possess them all):
   they do not produce biogenic amine from the aminated precursors,
   they do not degrade the glycerol, and
   they do not degrade the tartaric acid.

The bacterial preparations used in the method claimed are prepared from one or more strains belonging to the genuses *Lactobacillus* or *Pediococcus*, and may be selected from among the species *Lactobacillus plantarum, Lactobacillus casei, Lactobacillus delbrückii, Pediococcus acidilactici, Pediococcus damnceus, Pediococcus pentosaceus, Pediococcus parvulus* or *Pediococcus cerevisiae*.

In particular, one or more malolactic bacterial strains selected from the group composed of *Lactobacillus plantarum* DSM-9916, *Lactobacillus plantarum* CNCM I-2924 and *Pediococcus acidilactici* CNCM MA 18/5M may be used.

For example, it will be possible to add a preparation of malolactic bacteria comprising *Lactobacillus plantarum* CNCM I-2924 to a wine with a pH greater than or equal to 3.7, the concentration in alcohol of which is greater than 11%.

It will also be possible to inoculate a wine with a pH greater than or equal to 3.7, the concentration in alcohol of which is greater than 12%, with a preparation of malolactic bacteria, comprising *Lactobacillus plantarum* DSM-9916 or *Pediococcus acidilactici* CNCM MA 18/5M, or a mixture of these two strains.

Economically acceptable concentrations are in the order of $5.10^5$ to $5.10^7$ UFC/ml wine. Preferably, the wine is inoculated with $2.10^6$ UFC/ml. The lactic bacteria or the preparations of lactic bacteria are introduced directly into the fermentation medium without a prior acclimatisation stage. When the bacteria are added into the wine in the freeze-dried form, they undergo simple rehydration for about twenty minutes.

Finally, the present invention relates to a mature wine obtained by means of a preparation of lactic bacteria such as previously described or by means of the method which is the subject-matter of the invention.

The following examples will permit the achievement of the invention and the results obtained to be illustrated in greater detail.

EXAMPLE 1

Procedure for Selecting the Strains

A screening of natural strains of lactic bacteria arising from fermented wines or fermented fruit juices has been carried out. Isolates of natural lactic bacteria have been subjected to selection pressures according to the following criteria:
- Resistance to alcohol levels ≧10%
- Growth at low temperature (15° C.)
- No formation of biogenic amines
- No degradation of the glycerol
- No degradation of the tartaric acid

EXAMPLE 2

Determination of the Resistance to Ethanol

The malolactic bacteria are cultivated in a CMB medium. The pH of the medium is adjusted to 3.5 with 6N soda. The test tubes are filled with 5 ml of CMB medium and then autoclaved for 15 minutes at 121° C. After cooling, the alcohol levels are adjusted with pure ethanol to: 4%, 6%, 8%, 10%, 12% and 14%. The tubes are inoculated at 0.5% with an MRS culture cultivated for 48 h (Garvie, 1967, J. gen. Microbiol., Vol. 48, pp. 431-438). The growth is followed by measuring the turbidity at 600 nm after 3 weeks.

EXAMPLE 3

Determination of the Growth at Low Temperature

The growth at low temperature is tested in the same medium in accordance with the same procedure as that used for the determination of the resistance to alcohol described in Example 1. The growth is followed by measuring the turbidity at 600 nm after 3 weeks.

EXAMPLE 4

Screening for Production of Biogenic Amines from Aminated Acids

The selection of strains not producing biogenic amines was carried out by culture on a model MECM medium. The biogenic amines which were researched are those found most often in large quantity in wines: histamine, tyramine, putrescine and cadaverine. To select the strains not producing biogenic amines, these strains are cultivated on a model MECM medium supplemented with aminated acid precursors, namely histidine for the histamine, tyrosine for the tyramine, ornithine for the putrescine and lysine for the cadaverine.

| Composition of the model medium | Concentrations (g/l) |
| --- | --- |
| Tryptone | 10.0 |
| Yeast extract | 4.0 |
| Tween 80 | 1.0 |
| MgSO$_4$, 7 H$_2$O | 0.2 |
| MnSO$_4$, 4 H$_2$O | 0.05 |
| Calcium pantothenate | 0.01 |
| Glucose | 5.0 |
| Fructose | 5.0 |
| L-malic acid | 4.0 |

The pH is adjusted to 5.0 with HCl or NaOH, and the medium is autoclaved at 115° C. for 30 min. A mother solution of aminated acid precursors at 100 mg/l, sterilised by filtration, is added to the model medium. The final concentration of the supplemented model medium is:

| | |
| --- | --- |
| histidine | 10 mg/l |
| tyrosine | 10 mg/l |
| ornithine | 10 mg/l |
| lysine | 10 mg/l |

Pre-cultures of the lactic bacterial strains are produced in an MRS medium, then the cells are washed in a phosphate pad, and put back in suspension in the same volume of phosphate pad. The supplemented model medium is then inoculated at 1% with the strains to be tested. After the MLF is achieved (degradation of the malic acid), the samples are centrifuged, and the supernatants are frozen for analysis of the biogenic amines. Only the bacteria which do not form biogenic amines from the aminated acid precursors are retained.

EXAMPLE 5

Control of the Metabolism of the Glycerol and the Tartaric Acid

The study of the degradation of the tartaric acid and the glycerol is carried out in the MECMb medium, as follows:

| Composition of the MECMb medium | Concentration (g/l) |
| --- | --- |
| Tryptone | 10.0 |
| Yeast extract | 4.0 |
| Tween 80 | 1.0 |
| MgSO$_4$, 7 H$_2$O | 0.2 |
| MnSO$_4$, 4 H$_2$O | 0.05 |
| Calcium pantothenate | 0.01 |

The various following components are added to the MECMb medium to obtain different supplemented media:

| Compound | Concentration (g/l) |
| --- | --- |
| Glucose | 5.0 |
| Fructose | 5.0 |
| Glycerol | 5.0 |
| TMC: tartaric acid + malic acid + citric acid: | |
| Tartaric acid | 7.0 |
| Malic acid | 4.0 |
| Citric acid | 0.4 |

The degradation is tested in the following different combinations:

| Combination | Medium |
|---|---|
| 1 | MECMb |
| 2 | MECMb + TMC |
| 3 | MECMb + TMC + glucose |
| 4 | MECMb + TMC + fructose |
| 5 | MECMb + TMC + glycerol |
| 6 | MECMb + TMC + glucose + fructose + glycerol |

The bacteria, previously cultivated in the MRS medium, are washed and are used to inoculate the supplemented MECMb media at 1% (v:v). The cultures are incubated at 28° C. for 7-15 days, and the metabolites formed are analysed. Only the bacteria which degrade neither the tartaric acid nor the glycerol are retained.

EXAMPLE 6

Freeze-Drying Tests

The strains which have given a positive response to all of the selection criteria are tested with a view to production in the freeze-dried form. Two strains of *Lactobacillus plantarum* and one *Pediococcus* strain with the given characteristics were produced in the freeze-dried form for direct inoculation of the wines. The strain *Lactobacillus plantarum* DSM 9916 was isolated in a Californian Chardonnay wine, and the strain *Lactobacillus plantarum* CNCM I-2924 was isolated from a must of fruits which is intended to be distilled and was preserved by the addition of acid and $SO_2$.

EXAMPLE 7

Tolerance to Alcohol

The tolerance to ethanol was tested in the CMB medium for the following strains:
- the 2 selected strains of *Lactobacillus plantarum* CNCM I-2924 and DSM-9916,
- the selected strain of *Pediococcus acidilactici* CNCM MA 18/5M,
- a commercial strain of *Lactobacillus plantarum* (Viniflora) recommended for the inoculation of juice,
- the strain of *Lactobacillus plantarum* CNCM MA 18/5U, marketed for animal nutrition,
- the strain of *Lactobacillus casei* CNCM MA 542/2V, marketed for human nutrition, and
- the strain of *Oenococcus oeni* EQ54, marketed by Lallemand for direct sowing.

The cells were cultivated on CMB medium containing 0%, 4%, 6%, 8%, 10%, 12% and 14% of ethylic alcohol. The bacterial growth was determined at 21 days by spectrophotometric measurement of the optical density OD at 600 nm.

The tolerance to alcohol TA(x) of the strains in the presence of a quantity of alcohol x % is illustrated by the survival rate after 21 days in an alcoholised medium relative to the survival rate after 21 days in a medium without alcohol.

$TA(x)$=OD at $x$ % alcohol/OD at 0% alcohol

The results are shown in Table 1.

TABLE 1

| | Survival rate (%) in alcohol contents | | | | | |
|---|---|---|---|---|---|---|
| Strains | 4% | 6% | 8% | 10% | 12% | 14% |
| *L. pl.* CNCM I-2924 | 90 | 76 | 71 | 66 | 62 | 3 |
| *L. pl.* DSM-9916 | 88 | 84 | 71 | 68 | 57 | 3 |
| *P. acid* CNCM-MA18/5M | 114 | 106 | 102 | 71 | 46 | 8 |
| *L. pl.* Viniflora | 119 | 96 | 75 | 41 | 6 | 6 |
| *L. pl.* CNCM MA 18/5U | 82 | 68 | 52 | 25 | 6 | 4 |
| *L. cas.* CNCM MA 542/2V | 96 | 134 | 78 | 10 | 7 | 7 |
| *Oe. Oeni* EQ54 | 100 | 100 | 95 | 87 | 78 | 77 |

Among the strains *Lactobacillus plantarum* and *Pediococcus acidilactici*, only the selected strains of *L. plantarum* DSM-9916 and CNCM I-2924 and the strain *P. acidilactici* CNCM-MA 18/5M have a survival rate greater than 50% after 21 days in a medium containing 10% alcohol, and can be developed at concentrations of alcohol greater than 12%. These values are also achieved with the strain *Oe. oeni* EQ54.

EXAMPLE 8

Degradation of Malic Acid by *L. plantarum* CNCM I-2924

The MLF was achieved by means of the strain *L. plantarum* CNCM I-2924 by direct inoculation in the freeze-dried form, at the level of $2.0.10^6$ UFC/ml, after completion of the alcoholic fermentation in the following wines:
Test wine pH=3.6
Wine from the Vignerons de Buzet, pH=3.54
The tests are carried out in the laboratory, in 200 ml flagons.
Preparation of the Test Wine
The test wine was manufactured from commercial grape juice in three stages:
A) Winemaking:
1—The juice is supplemented by 70 g/l of dextrose.
2—The juice is inoculated with 20 g/hl of active dry yeast Lalvin CY3079; the yeast is previously rehydrated in a small volume of juice at 30° C. for 30 minutes.
3—The fermentation is conducted at a temperature of between 20 and 25° C.
4—After a week, the concentration of residual sugars is measured. If the concentration of residual sugars is lower than 2 g/l, the wine is clarified.
B) Clarification:
1—The wine is clarified by centrifugalisation (8500 rpm, 10 min)
2—The wine is put at 4° C. for 8 days.
3—The crystals of tartaric acid are eliminated by centrifugalisation (8500 rpm, 10 min)
C) Standardisation:
The wine is analysed after alcoholic fermentation and before inoculation of freeze-dried preparations of *L. plantarum* DSM-9916, the pH is adjusted to 3.6, the malic acid content is brought to 5 g/l. The test wine thus obtained has the following characteristics:

| | |
|---|---|
| Alcohol (% by vol.) | 11.94 |
| Residual sugars (g/l) | 0.0 |
| Free $SO_2$ (mg/l) | 4 |
| Total $SO_2$ (mg/l) | 5 |
| Acetic acid (g/l) | 0.23 |
| pH | 3.18 adjusted to 3.6 |

-continued

| | |
|---|---|
| Total acidity (g/l $H_2SO_4$) | 5.0 |
| Malic acid (g/l) | 3.1 brought to 5.0 |

Red Wine (Vignerons de Buzet)

The red wine used is a commercial wine produced by the Vignerons de Buzet. The wine has only been filtered and kept at 4° C.

The wine was analysed after alcoholic fermentation and before inoculation of freeze-dried preparations of *L. plantarum* DSM-9916.

| | |
|---|---|
| Alcohol (% by vol.) | 12.30 |
| Residual sugars (g/l) | 0.5 |
| Free $SO_2$ (mg/l) | 4 |
| Total $SO_2$ (mg/l) | 5 |
| Acetic acid (g/l) | 0.17 |
| pH | 3.54 |
| Total acidity (g/l $H_2SO_4$) | 3.6 |
| Malic acid (g/l) | 1.5 |

The freeze-dried bacterial preparation is rehydrated in water at 22° C. for minutes. The solution is then added directly into the wine after alcoholic fermentation. The survival in the wine and the degradation of the malic acid are measured until the substrate is exhausted. For each wine, two tests were carried out. An unsown batch served as the control.

Survival Rate

Table 2 gives the results of the survival rates of *L. plantarum* CNCM I-2924, 2 days and 14 days after inoculation.

TABLE 2

| Wine | Inoculation (UFC/ml) | Population at D0 (UFC/ml) | Population at D2 (UFC/ml) | % survival at D2 | Population at D14 (UFC/ml) | % survival at D14 |
|---|---|---|---|---|---|---|
| Test | 2.0E6 | 2.1E6 | 1.9E6 | 90 | 1.8E6 | 86 |
| Test | 2.0E6 | 2.1E6 | 1.85E6 | 89 | 1.65E6 | 79 |
| Buzet | 2.0E6 | 1.9E6 | 1.6E6 | 84 | 1.7E6 | 89 |
| Buzet | 2.0E6 | 1.95E6 | 1.7E6 | 87 | 1.6E6 | 82 |

Degradation of Malic Acid

The dosing with malic acid is carried out for each test at regular intervals by means of a dosing kit (kit E 0139 068, Boehringer Mannheim, Germany).

FIG. 1 shows the kinetics of degradation of the malic acid in the test wine at pH=3.6, after inoculation of a freeze-dried preparation of *L. plantarum* CNCM I-2924.

Figure 2:
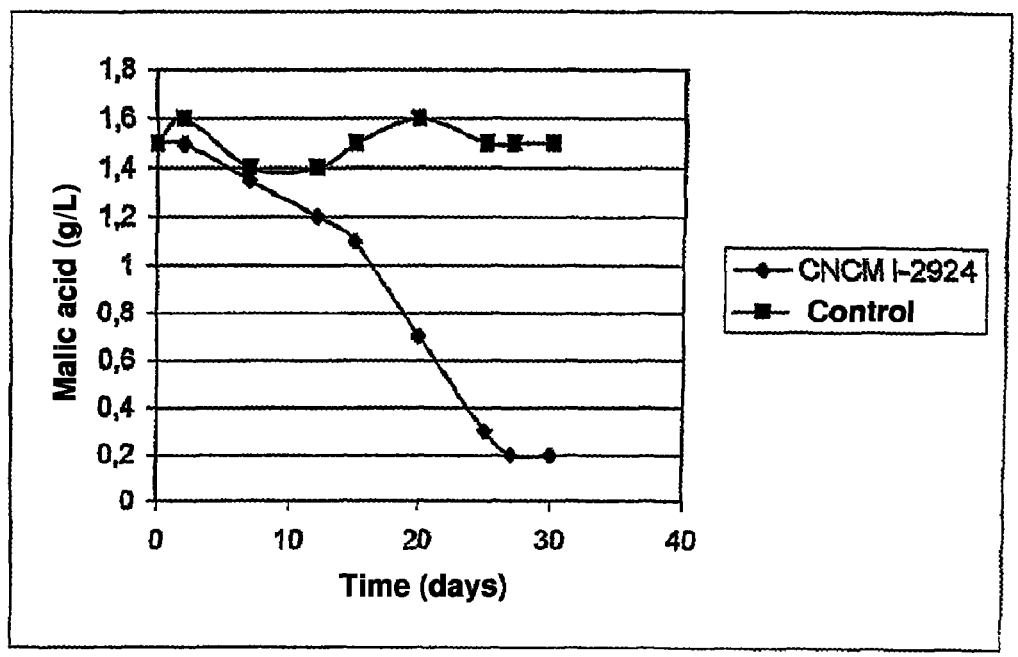
FIG. 2 shows the kinetics of degradation of the malic acid in the Buzet wine after inoculation with a freeze-dried preparation of L. plantarum CNCM I-2924.

FIG. 2 shows the kinetics of degradation of the malic acid in the Buzet wine after inoculation with a freeze-dried preparation of *L. plantarum* CNCM I-2924.

EXAMPLE 9

Degradation of Malic Acid by *L. plantarum* DSM-9916

The MLF was achieved by means of the strain *L. plantarum* DSM-9916 by direct inoculation in the freeze-dried form, at the level of $3.0.10^6$ UFC/ml, after completion of the alcoholic fermentation in the same red wine from the Vignerons de Buzet, at pH=3.54, as that used in the preceding Example. The Buzet wine was prepared as before and possesses the same chemical characteristics (see Example 8). The test was conducted in accordance with the same procedure.

Survival rate: Table 3 gives the results of the survival rates of *L. plantarum* CNCM I-2924, 2 days and 14 days after inoculation.

TABLE 3

| Wine | Inoculation (UFC/ml) | Population at D0 (UFC/ml) | Population at D2 (UFC/ml) | % survival at D2 | Population at D14 (UFC/ml) | % survival at D14 |
|---|---|---|---|---|---|---|
| Buzet | 3.0E6 | 2.3E6 | 2.3E6 | 97 | 1.8E6 | 78 |
| Buzet | 3.0E6 | 3.1E6 | 2.1E6 | 68 | 1.8E6 | 58 |

Figure 3:
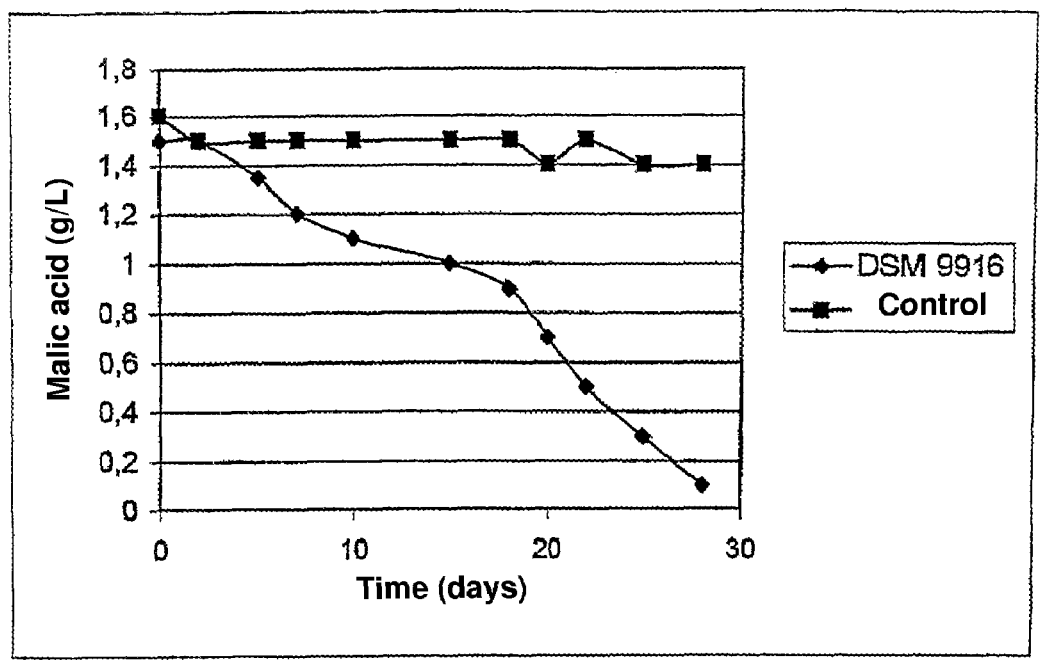
FIG. 3 shows the kinetics of degradation of the malic acid in the Buzet wine after inoculation of a freeze-dried preparation of L. plantarum DSM-9916.

Degradation of malic acid: The dosing with malic acid is carried out for each test at regular intervals by means of a dosing kit (kit E 0139 068, Boehringer Mannheim, Germany). FIG. 3 shows the kinetics of degradation of the malic acid in the Buzet wine after inoculation of a freeze-dried preparation of *L. plantarum* DSM-9916.

EXAMPLE 10

Degradation of Malic Acid in a Cabernet Wine by *L. plantarum* DSM 9916 and *P. acidilactici* CNCM MA-18/5M Comparison with *Oe. oeni* EQ54

The MLF was carried out in a Cabernet Sauvignon wine from Chile in 2002, with a pH of 3.7. The tests were conducted in four barrels of 225 l:
  wine sown by means of the strain *L. plantarum* DSM 9916,
  wine sown by means of the strain *P. acidilactici* CNCM MA-18/5M,
  wine sown by means of the strain *Oe. oeni* EQ54,
  control wine, not sown.

The wine was analysed after alcoholic fermentation and before inoculation of freeze-dried preparations of lactic bacteria.

| | |
|---|---|
| Alcohol (% by vol.) | 12.9 |
| Residual sugars (g/l) | 0.3 |
| Free $SO_2$ (mg/l) | 6 |
| Total $SO_2$ (mg/l) | 13 |
| pH | 3.7 |
| Malic acid (g/l) | 1.90 |
| Lactic acid (g/l) | 0.08 |

Figure 4:
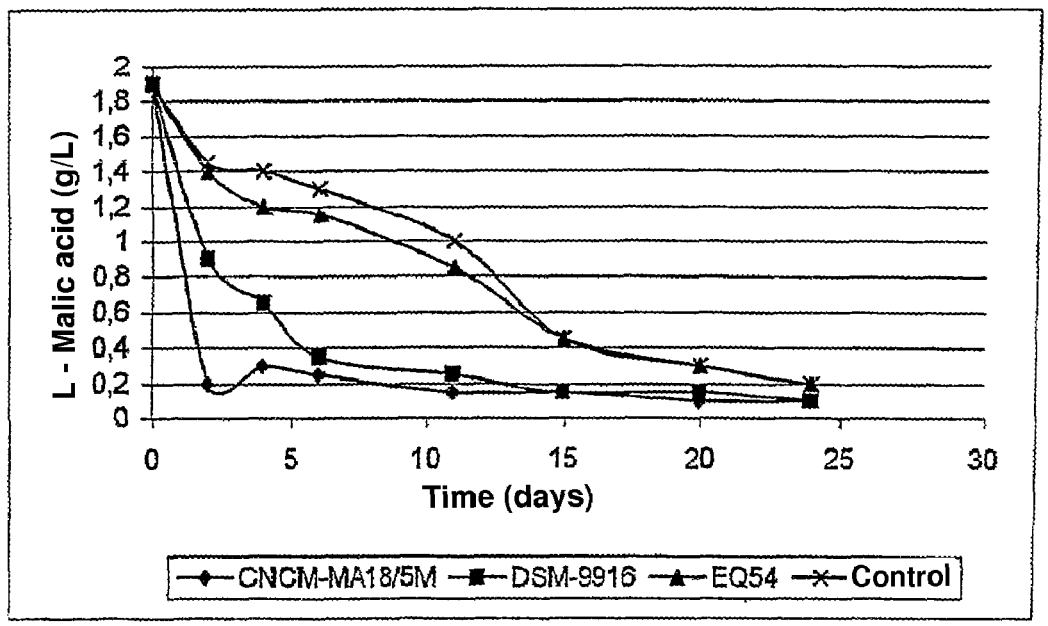
FIG. 4 illustrates the kinetics of degradation of the malic acid in wine after completion of the alcoholic fermentation and inoculation with strains L. plantarum DSM 9916, P. acidilactici CNCM MA-18/5M and Oe. oeni EQ54 in the freeze-dried form.

The strains were inoculated in the freeze-dried form at the level of $2.0.10^6$ UFC/ml, at 18° C., directly into the wine after completion of the alcoholic fermentation. The dosing with malic acid was carried out for each test at regular intervals by means of a dosing kit (kit E 0139 068, Boehringer Mannheim, Germany). The results are illustrated in FIG. 4.

The kinetics of degradation of the malic acid indicate a good implantation of the strains DSM 9916 and CNCM MA-18/5M, and an early and efficient start-up of the fermentation activity. The control test shows that, in this wine with a relatively high pH (pH=3.7), the MLF is started spontaneously from the first days. In the test carried out with sowing by *Oe. oeni*, the kinetics of degradation of the malic acid are very close to those of the control test, and this means that undesirable indigenous strains have developed quite rapidly to supplant *Oe. oeni*. The control of the MLF, guaranteeing fermentation safety, was only obtained with the strains *L. plantarum* DSM 9916 and *P. acidilactici* CNCM MA-18/5M.

EXAMPLE 11

Degradation of Malic Acid in a Tempranillo Wine by L. plantarum CNCM I-2924

Comparison with Oe. oeni EQ54

The MLF was carried out in a Tempranillo wine from Rioja (Spain) in 2002, with a pH of 3.9. In the wines of this region, a spontaneous start-up of the MLF often occurs, and this is generally translated by high levels of biogenic amines. The tests were conducted in 3 barrels of 225 l:
- wine sown by means of the strain L. plantarum CNCM I-2924,
- wine sown by means of the strain Oe. oeni EQ54,
- control wine, not sown.

The wine was analysed after alcoholic fermentation and before inoculation of freeze-dried preparations of lactic bacteria.

| | |
|---|---|
| Alcohol (% by vol.) | 11.98 |
| Residual sugars (g/l) | 0.2 |
| Free $SO_2$ (mg/l) | 4 |
| Total $SO_2$ (mg/l) | 11 |
| pH | 3.9 |
| Malic acid (g/l) | 2.35 |
| Lactic acid (g/l) | 0.05 |

Figure 5:
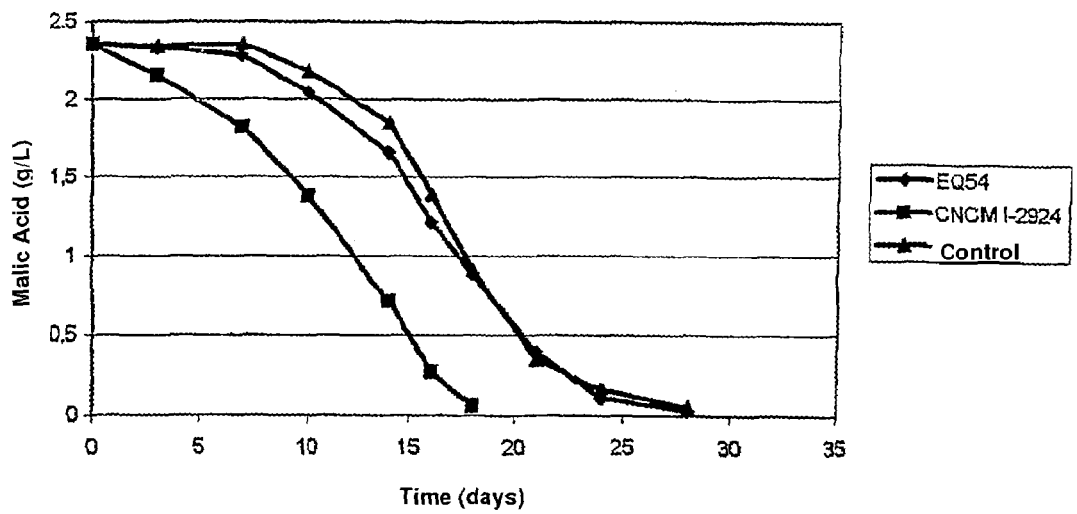
FIG. 5 illustrates the kinetics of degradation of the malic acid in wine after completion of the alcoholic fermentation and inoculation with strains L. plantarum CNCM I-2924 and Oe. oeni EQ54 in the freeze-dried form.
Figure 6:
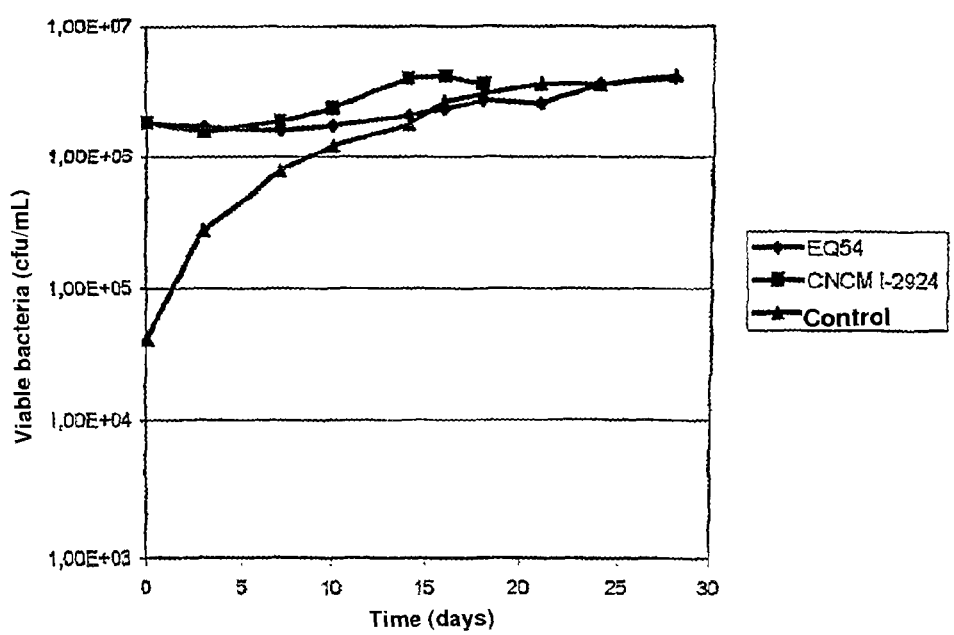
FIG. 6 illustrates the cellular growth of the wine described in FIG. 5, which after completion of the alcoholic fermentation and innoculation with strains *L. plantarum* CNCM I-2924 and *Oe. oeni* EQ54 in the freeze-dried form.

The strains were inoculated directly in the freeze-dried form at the level of $2.0.10^6$ UFC/ml, at 18° C., after completion of the alcoholic fermentation. The dosing with malic acid is carried out for each test at regular intervals by means of a dosing kit (kit E 0139 068, Boehringer Mannheim, Germany). In parallel, the bacterial growth was measured in the three vats. The results are illustrated in FIGS. 5 and 6.

The kinetics of degradation of the malic acid (FIG. 5) show a rapid induction of the fermentation with L. plantarum CNCM I-2924. On the other hand, the MLF only starts after 10 days in the vat sown with Oe. oeni EQ54 and in the control vat: no difference is observed between these two tests, and this means that undesirable indigenous strains have developed quite rapidly to supplant Oe. oeni.

Following up the cellular growth (FIG. 6) reveals, moreover, that the population of Oe. oeni EQ54 did not fall at the time of inoculation into the wine and remained at the same level as the population of L. plantarum. The retardation of the start-up of the MLF by Oe. oeni, despite a satisfactory a priori cellular concentration, can be attributed to an inability to induce fermentation activity in conditions of strong alcoholic concentration and high pH. The survival rate does not constitute, in this case, the decisive criterion to ensure efficient control of the MLF.

The invention claimed is:

1. A method of converting malic acid into lactic acid in a wine which has a pH greater than or equal to 3.5, said method consisting of introducing a preparation of lactic bacteria strains belonging to the genus Lactobacillus or Pediococcus and affecting the conversion of malic acid to lactic acid, directly in the dried, freeze-dried or frozen state, into said wine, at a concentration of between $10^6$ and $5.10^7$ UFC/ml, at a temperature greater than or equal to 18° C., when the alcohol degree has reached at least 10%, and of maintaining the wine in conditions which permit the development of malolactic fermentation, to obtain a mature wine which has a malic acid content lower than 0.2 g/l.

2. A method of converting malic acid into lactic acid in a wine which has a pH greater than or equal to 3.5, said method consisting of introducing a preparation of lactic bacteria comprising one or more strains, which (i) belong to the genus Lactobacillus or Pediococcus, (ii) affect the conversion of malic acid to lactic acid, and (iii) are homofermentary, directly in the dried, freeze-dried or frozen state, into said wine, at a concentration of between $10^6$ and $5.10^7$ UFC/ml, at a temperature greater than or equal to 18° C., when the alcohol degree has reached at least 5%, and of maintaining the wine in conditions which permit the development of malolactic fermentation, to obtain a mature wine which has a malic acid content lower than 0.2 g/l.

3. The method of converting malic acid into lactic acid according to claim 1, in which said preparation possesses in addition one or more of the following characteristics:
- said preparation does not produce biogenic amine from aminated precursors,
- said preparation does not degrade glycerol, and
- said preparation does not degrade tartaric acid.

4. The method of converting malic acid into lactic acid according to claim 1, in which said preparation comprises one or more malolactic bacterial strains selected from the group consisting of Lactobacillus plantarum, Lactobacillus casei, Lactobacillus delbrückii, Pediococcus acidilactici, Pediococcus damnceus, Pediococcus pentosaceus, Pediococcus parvulus, and Pediococcus cerevisiae.

5. The method of converting malic acid into lactic acid according to claim 2, in which said preparation comprises one or more malolactic bacterial strains selected from the group consisting of Lactobacillus plantarum DSM-9916, Lactobacillus plantarum CNCM I-2924 and Pediococcus acidilactici CNCM MA 18/5M.

6. The method according to claim 5, in which a preparation of malolactic bacteria comprising Lactobacillus plantarum CNCM I-2924 is added to a wine with a pH greater than or equal to 3.9 and with an alcohol concentration of greater than 11%.

7. The method according to claim 5, in which a preparation of malolactic bacteria, comprising Lactobacillus plantarum DSM-9916 or Pediococcus acidilactici CNCM MA 18/5M or a mixture of these, is added to a wine with a pH greater than or equal to 3.7 and with an alcohol concentration of greater than 12%.

* * * * *